United States Patent [19]

Thompson et al.

[11] 4,080,836
[45] Mar. 28, 1978

[54] METHOD OF MEASURING STRESS IN A MATERIAL

[75] Inventors: Robert B. Thompson; George A. Alers, both of Thousand Oaks, Calif.

[73] Assignee: Rockwell International Corporation, El Segundo, Calif.

[21] Appl. No.: 774,834

[22] Filed: Mar. 7, 1977

[51] Int. Cl.² .................... G01N 29/00; G01B 7/16
[52] U.S. Cl. ........................................ 73/597; 73/643; 73/88 R
[58] Field of Search ............... 73/67.5, 67.6, 88 R, 73/560

[56] References Cited

U.S. PATENT DOCUMENTS

| | | | |
|---|---|---|---|
| 3,460,063 | 8/1969 | Houck et al. | 73/67.8 R X |
| 3,550,435 | 12/1970 | Kaule | 73/67.8 R |
| 3,587,297 | 6/1971 | Kammer | 73/67.6 |
| 3,786,672 | 1/1974 | Gaerttner | 73/67.5 R |
| 3,812,709 | 5/1974 | Benson et al. | 73/67.5 R |

OTHER PUBLICATIONS

R. T. Smith — "Stress Induced Anisotropy in Solids/-The Acousto-Elastic Effect" — *Ultrasonics* — Jul.—Sep., 1963, pp. 139–144.

*Primary Examiner*—Charles A. Ruehl
*Attorney, Agent, or Firm*—L. Lee Humphries; Craig O. Malin

[57] ABSTRACT

Stress in a material is measured using electromagnetically generated, transverse elastic waves. A correlation is known to exist between the difference in velocity of orthogonally polarized transverse waves in the type material being measured and stress in the material. An electromagnetic transducer is used to generate orthogonally polarized waves traveling through the part at different velocities as a result of anisotropic stress in the part. The difference in velocity between the polarized waves is measured and compared to the correlation to obtain the stress existing in the part.

2 Claims, 12 Drawing Figures

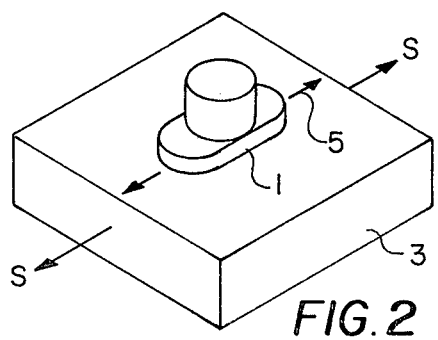
FIG.2
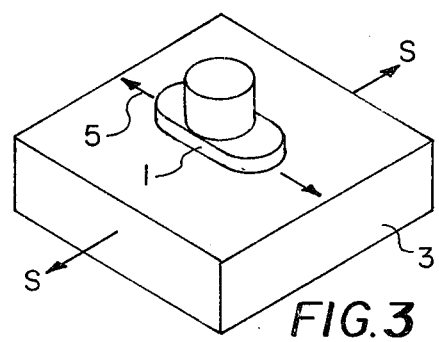
FIG.3
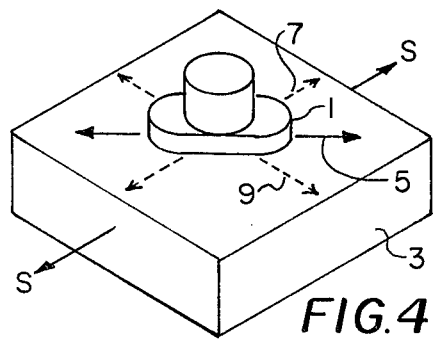
FIG.4
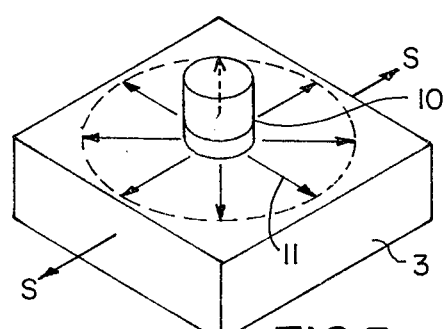
FIG.5
FIG.6
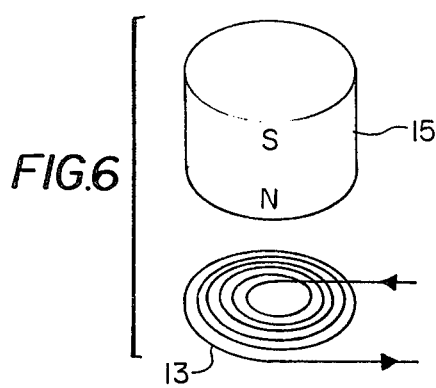
FIG.9
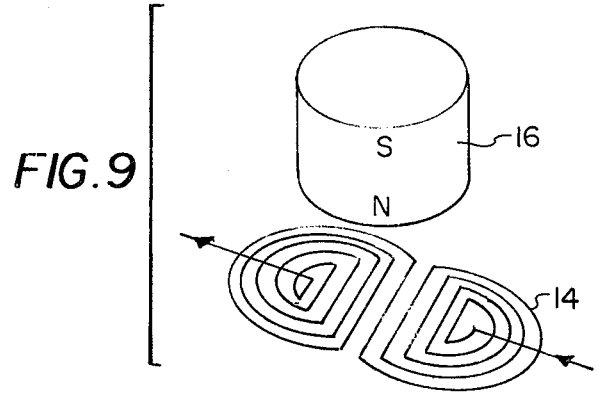
FIG.7
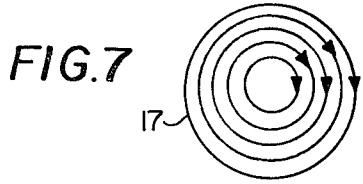
FIG.10
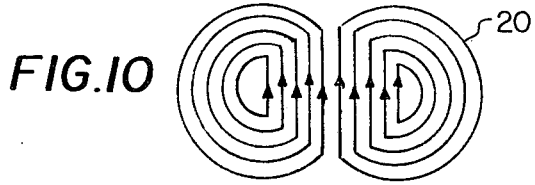
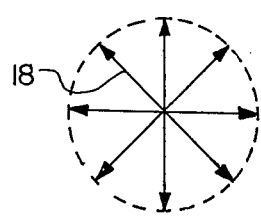
FIG.8
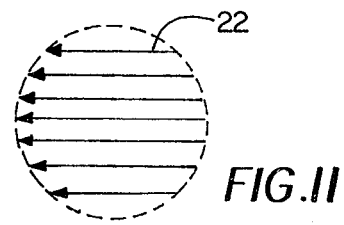
FIG.11

METHOD OF MEASURING STRESS IN A MATERIAL

BACKGROUND OF THE INVENTION

A. Field of the Invention

This invention relates to the field of non-destructive evaluation of stress in materials, and more particularly to the use of elastic waves, sometimes called ultrasonic waves, for measuring stress.

B. Description of the Prior Art

The only well-developed method of nondestructively measuring stress in materials is the x-ray diffraction method. This method depends upon the measurement of distances between planes of atoms by exposing the material to x-rays and measuring the diffraction of the x-rays. Application of this method is severely restricted by the fundamental inability of x-rays to probe deeper than about a thousand atomic layers into the material, and by the method's total inapplicability to non-crystalline materials.

Other possible methods of measuring stress utilizing ultrasonics, electromagnetics, or nuclear hyperfine effects are in a very early stage of development. The present invention is limited to ultrasonic methods of measuring stress. All ultrasonic methods depend in principle upon the fact that the velocity of propagation of ultrasound (elastic waves) in a solid medium is influenced by the state of strain of the medium. Although the effect is small, its detection and measurement are within the present state of the ultrasonic art.

However, the velocity of sound is also affected by numerous other factors related to the condition of the material such as its microstructure, heat treatment, grain orientation, density, and homogeneity. Therefore, the determination of the absolute velocity of sound in a material does not give an accurate indication of stress in the material unless standards which accurately represent all the other velocity-affecting conditions are available. To overcome this problem with absolute velocity determination, a known technique called shear wave birefringence is used. See, for example, "Shear Wave Birefringence," by N. N. Hsu, in *Proceedings of a Workshop on Nondestructive Evaluation of Residual Stress*, Aug. 13-14, 1975, published by NTIAC, San Antonio, Texas. This technique is based upon measuring the difference in velocity of piezoelectrically generated shear waves which are orthongonally polarized by the anisotropic stress existing within the material. According to this technique, only the difference in velocity between two shear waves is measured. Since this difference in velocity is caused primarily by the difference in stress in two orthogonal directions within the material, the effect of material condition can be minimized or at least accounted for.

According to the prior art, piezoelectric transducers are required to inject ultrasonic waves into the material being measured. These transducers utilize an oriented crystal which is strained along a particular crystallographic axis in response to an electric field applied to the crystal (the piezoelectric effect). Consequently, the piezoelectric transducer must be rigidly attached or coupled by a very viscous fluid or a solid bond to the material being evaluated in order to inject an ultrasonic wave into the material. Additionally, since motion of the piezoelectric is generated only along a specific crystallographic axis, single piezoelectric crystals can create a driving force on the surface of the material in only a single direction as defined by the crystal orientation.

If a uniaxial stress exists in the material being measured, and if a prior art piezoelectric transducer is oriented parallel or transverse to the stress; then the transverse wave generated by the transducer will not be polarized (or decomposed) into two separate, orthogonally polarized shear waves. Rather, only a single transverse wave oriented in the same direction as the transducer will be created. To generate a second wave having a different velocity, the transducer can be rotated 90° to obtain a second wave at 90° to the first wave; or the transducer can be rotated less than 90° in order to create two orthogonally polarized waves as discussed earlier. Because the piezoelectric transducer must be in rigid contact or otherwise physically coupled to the material, rotation of the transducer to obtain a second wave or a pair of orthogonally polarized shear waves of measurable magnitude is very inconvenient.

SUMMARY OF THE INVENTION

It is an object of the invention to provide an improved method of measuring stress in a material.

It is an object of the invention to provide an improved method of measuring the orientation of stress in a material.

It is an object of the invention to provide a method of measuring stress in a material which method is more convenient than prior methods.

It is an object of the invention to provide a method of measuring stress in a material without requiring physical contact with the material.

It is an object of the invention to provide a method of measuring stress in a material without requiring any orientation of the measuring device with respect to the direction of stress in the material.

According to the invention, stress in a material is measured using electromagnetically generated, transverse elastic waves. A correlation is obtained between the difference in velocity of orthogonally polarized transverse waves in the type material being measured and stress in the material. An electromagnetic transducer is then used to generate orthogonally polarized waves traveling through the part at different velocities as a result of anisotropic stress in the part. The difference in velocity between the polarized waves is measured and compared to the correlation to obtain the difference in stress existing in the part.

These and other objects and features of the present invention will be apparent from the following detailed description, taken with reference to the accompanying drawings.

BRIEF DESCRIPTION OF THE DRAWINGS

FIG. 2 is an illustration of an electromagnetic transducer oriented parallel to the stress in a part;

FIG. 3 is an illustration of an electromagnetic transducer oriented transverse to the stress in a part;

FIG. 4 is an illustration of an electromagnetic transducer oriented at an angle between 0° and 90° to the stress;

FIG. 5 is an illustration of a radial electromagnetic transducer positioned on a part;

FIG. 6 is an exploded view of an electromagnetic transducer for generating radially polarized driving forces in a part;

FIG. 7 shows the eddy currents created in a part by the transducer of FIG. 6;

FIG. 8 shows the radially polarized driving forces created in a part by the transducer of FIG. 6;

FIG. 9 is an exploded view of an electromagnetic transducer for generating unidirectional driving forces in a part;

FIG. 10 shows the eddy currents created in a part by the transducer of FIG. 9;

FIG. 11 shows the unidirectional driving forces created by the transducer of FIG. 10;

DESCRIPTION OF THE PREFERRED EMBODIMENT

Elastic waves can be propagated through a solid in a longitudinal mode in which the displacement of the particles in the solid are in the same direction as the propagation of the wave, and in a transverse mode in which the displacement of the particles are transverse to the direction of propagation of the wave. Additionally, the transverse mode can be polarized in a transverse direction about the direction of propagation.

Figure 1:
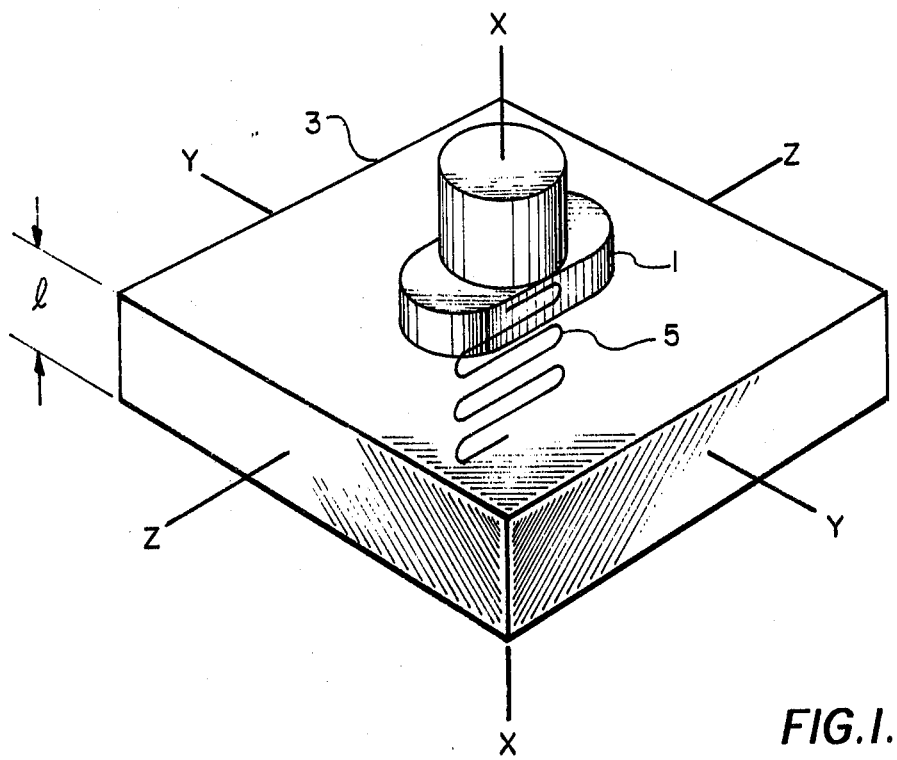
FIG. 1 is a perspective view of an electromagnetic transducer generating a transverse wave according to the invention.

The technique known as shear wave birefringence utilizes only the transverse wave which is also known as the shear wave. FIG. 1 shows an electromagnetic transducer 1 mounted on a test block 3 which has a thickness "l". A current of suitable frequency is applied to the coil of electromagnetic transducer 1 to generate a transverse, or shear wave, 5 traveling through the thickness "l" of the block 3 in direction X. When shear wave 5 reaches the opposite face of block 3, it is reflected back to transducer 1 which picks up the returning signal and can be used to determine the time required for the wave to make the round trip (2"l").

The transducer 1 shown in FIG. 1 is oriented so that forces are produced on the surface of block 3 in the Z direction. If the test block material is isotropic and unstressed, the resulting shear wave 5 would travel with a velocity $V_o$ through the block polarized in the same direction (Z direction) as the orientation of the transducer 1. When the test block is placed in compression along the Z axis, the velocity of wave 5 is increased slightly in most materials. Conversely, when tension is applied along the Z direction, the velocity of wave 5 is decreased slightly. However, in both cases, the polarization of wave 5 remains the same provided that the stress in the material is parallel to the wave polarization.

If, however, the stress in block 3 is neither parallel nor perpendicular to the orientation of the transducer 1, then the shear wave polarization is changed. Instead, it is decomposed into two waves polarized parallel and perpendicular to the applied stress. Because these two polarized waves are travelling in material under different conditions of stress, their velocity will be different. Transducer 1 can readily detect this difference in velocity which is directly related to the difference in stress in the material.

FIGS. 2-4 show three possible orientations of an electromagnetic transducer 1 with respect to the principal stress "S." In the orientation of FIG. 2, shear wave 5 will not be decomposed into two components because the particles in the material are moving parallel to the applied stress and cannot detect the anisotropic stress in the block. Likewise for the orientation perpendicular to the stress as shown in FIG. 3. Thus, if the transducer is in either of these orientations, only a single wave velocity can be measured. If the transducer is then rotated 90°, a second wave velocity will be obtained and the difference in velocity can be used to obtain the stress in the material according to the method of shear wave birefringence.

However, if transducer 1 is oriented on block 3 at an angle other than 0° or 90° to the principle axis of stress S, as shown in FIG. 4, then the shear wave decomposes into two orthogonally polarized waves 7, 9. As discussed earlier, these two waves travel at different velocities due to the different stresses in the direction in which they are polarized. The difference in velocity can be compared to a previously obtained correlation between velocity and stress in order to determine the stress "S" in block 3.

There are at least two advantages to generating the waves electromagnetically rather than with a piezoelectric transducer. First, it is possible to simultaneously create a plurality of driving forces in different directions with an electromagnetic transducer, whereas only a single driving force can be generated with a piezoelectric transducer. This eliminates any need to rotate the transducer to obtain two distinct, orthogonally polarized shear waves. FIG. 5 shows a radial electromagnetic transducer 10 which creates radial driving forces 11 on the surface of block 3. Under the influence of a principal stress "S," radial waves created by driving forces 11 will be decomposed into two waves polarized at right angle to each other, each traveling at a speed determined by the stress in the polarized axes. The difference in speed of these two waves can then be used to determine the difference in stress along the axes of principal stress.

A second advantage of electromagnetic transducers is that they generate waves in the material without any contact or physical coupling required. This greatly increases the convenience of the test, particularly for testing stressed parts under actual operating conditions.

FIGS. 6-8 shows the design of a radial electromagnetic transducer suitable for generating radial driving stresses for use in one embodiment of the method of the invention. FIG. 6 is an exploded perspective view of a flat, spiral coil 13 placed under a permanent magnet 15. When a current of suitable frequency is passed through coil 13, eddy currents 17 are created in the material being tested as shown in FIG. 7. These eddy currents interact with the field from permanent magnet 15 to create radially polarized driving forces 18 at the surface of the material as shown in FIG. 8. These forces cause transverse waves to radiate into the material and to propagate through the material with polarizations and speeds determined by the material's conditions.

FIG. 9–11 shows the design of a unidirectional electromagnetic transducer suitable for generating unidirectional driving stresses for use in a second embodiment of the method of the invention. FIG. 9 is an exploded perspective view of a specially constructed coil 14 placed under a permanent magnet 16. When a current of suitable frequency is passed through coil 14, eddy currents 20 are created in the material being tested as shown in FIG. 48. These eddy currents 20 interact with the field from permanent magnet 16 to create unidirectional driving forces 22 at the surface of the material as shown in FIG. 11. These forces cause transverse waves to radiate into the material and to propogate through the material with polarizations and speeds determined by the material's condition.

Figure 12:
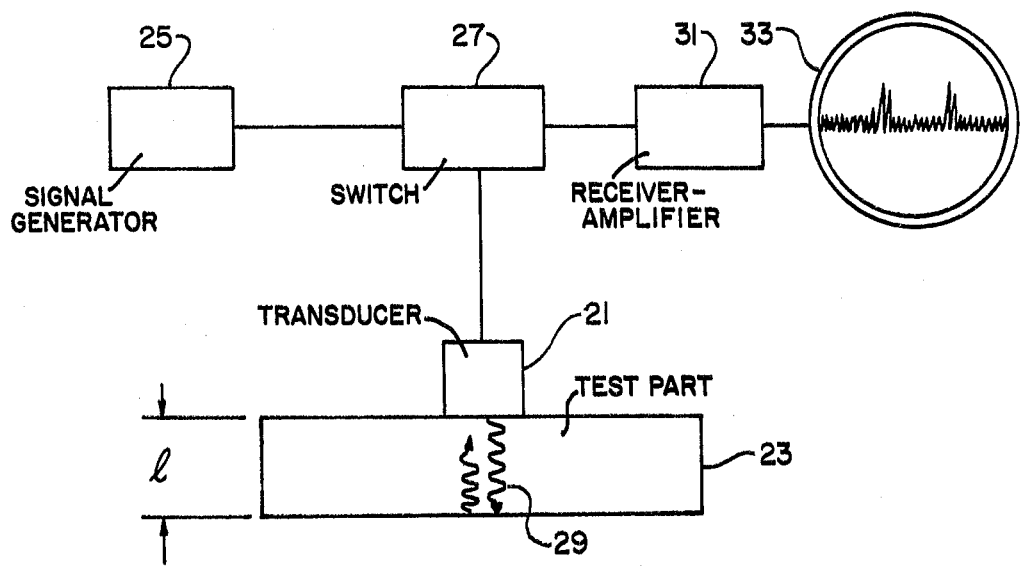
FIG. 12 is a schematic arrangement of components utilized to practice the method according to the invention.

FIG. 12 is a schematic wiring diagram showing individually known electronic components in an arrangement suitable for practicing the method of the invention. Electromagnetic transducer 21 is placed adjacent the surface of the part 23 being inspected for stress. Signal generator 25 creates a signal which is directed by transmitter-receiver switch 27 to transducer 21 which then functions as a transmitter. This created a shear wave 29 which travels through the thickness "$l$" of part 29, reflects off the opposite side and is picked up by transducer 21 functioning as a receiver. The signal from transducer 21 is routed by switch 27 to a receiver-amplifier 31. The amplified signal is read out in a suitable device such as oscilliscope 33.

The difference in time required for differently polarized shear waves to make the round trip ($2l$) from the transducer 21 to the opposite side of the part 23 and back can be readily measured with great accuracy utilizing known ultrasonic techniques. The corresponding velocities can then be obtained simply by dividing the travel time into the distance traveled.

According to one technique, one or more short impulses are used to generate two differently polarized waves in the material. If a unidirectional transducer oriented as shown in FIGS. 2 or 3 is used, two impulses at different orientations are required to obtain the two differently polarized waves, as discussed before. However, if a transducer oriented as shown in FIG. 4 is used, or if a radial transducer (FIG. 5) is used, then only a single short impluse is required to generate the two waves. These two waves travel through an anisotropically stressed material at different speeds and therefore return to the transducer 21 at two different times. Their difference in travel time shows up as a pair of spaced peaks on oscilloscope 33 which can readily be converted to an equivalent difference in velocity, as follows:

$$\Delta V = \frac{2l}{t_y} - \frac{2l}{t_z}, \quad \Delta V = \frac{2l(t_z - t_y)}{t_y t_z}, \quad \text{or}$$

$$\frac{\Delta V}{V} \simeq \frac{t_z - t_y}{\bar{t}},$$

where:

$\Delta \bar{V}$ equals the difference in velocity of the two polarized waves,

V equals the typical velocity of shear waves in the material, $l$ equals the thickness of the part, $t_y$ and $t_z$ equal the time of arrival of respective shear waves, and $\bar{t}$ equals the average of $t_y$ and $t_z$.

A second, tone burst technique, utilizes the destructive interference of ultrasonic waves of different frequency to determine the difference in velocity between two polarized waves. This technique requires that the two differently polarized waves be generated simultaneously (FIG. 4 or 5). According to the tone burst technique, the frequency at which both polarized waves is transmitted is varied from a first frequency, $f_1$, of maximum destructive interference through a second frequency, $f_2$, of maximum constructive interference, to a third frequency, $f_3$, again of maximum destructive interference. The difference in velocity between the polarized waves can then be calculated from the difference in frequency, $\Delta f$, between the conditions for maximum destructive interference (equations 1 and 2) according to the following:

$$\frac{2lf_1}{V_y} = \frac{2lf_1}{V_z} + (2n + 1)\pi, \tag{1}$$

$$\frac{2lf_3}{V_y} = \frac{2lf_3}{V_z} + (2n + 3)\pi, \tag{2}$$

Substracting equation (1) from equation (2):

$$\frac{2l}{V_y}(\Delta f) = \frac{2l}{V_z}(\Delta f) + 2\pi,$$

$$2l\Delta f \frac{V_z - V_y}{V_y V_z} = 2\pi,$$

$$\Delta V = \frac{V_y V_z \pi}{l \Delta f},$$

$$\frac{\Delta V}{V} = \frac{V}{l} \frac{\pi}{\Delta f}.$$

According to the method of the invention, the change in velocity, $\Delta V$, as a function of stress (the value "K" in the equation below) is determined for the type of material being evaluated. This relationship can be expressed as:

$$\Delta V = K \Delta S + C \tag{3}$$

where:

$\Delta V$ is the difference in velocity between the orthogonally polarized shear waves, $\Delta S$ is the difference in stress in the direction of the principal stress axes, C is the value of $\Delta V$ when $\Delta S$ equals zero in the particular part being tested, and K is a constant for the type of material being tested.

The constant K is substantially the same for all materials of the same general composition. Examples of values of K which have been determined are: 0.014 in./sec/psi for 1018 steel and 0.037 in./sec/psi for 2024 aluminum alloy.

In equation (3) above, K is the slope of the line defining the function, and C is the intercept of the line with the axis representing $\Delta V$. C is influenced by the grain orientation, flow lines, inclusions, and other inhomogenuities of the particular part being tested. Its value is determined by testing an unstressed (or known stressed) area on the actual part or on a representative part.

After K and C have been determined for the material of the part being tested, the curve defined by equation (3) is constructed. Then $\Delta V$ is obtained for two orthogonally polarized transverse waves in the desired area on the part being tested. The $\Delta V$ obtained is compared to the correlation to obtain the difference in stress along the principal stress axes in the part. Because electromagnetic transducers can be constructed to create differently oriented driving forces simultaneously, orthogonally polarized elastic waves can be obtained readily without requiring rotation of the transducer. Additionally, electromagnetic transducers can be moved easily over the surface of the part to survey the stress pattern because the electromagnetic transducer does not have to be coupled physically to the part.

When a transducer such as shown in FIG. 3 is utilized, driving forces are created in all radial direction. Consequently, it is not necessary to rotate the transducer to obtain the maximum amplitudes of both orthogonally polarized waves produced by propagation through an anisotropically stressed material. However, the orientation of the principal stress axes cannot be obtained because rotation of the radially symmetrical transducer does not change the amplitude of either of the received waves.

If it is desired to obtain the orientation of the principal stress axis, then a transducer which generates a driving force of known orientation can be used. When such an oriented transducer is rotated, the amplitudes of the orthogonally polarized waves received after propagating through the material are changed. When the amplitude of one wave is at a maximum, the other is at a minimum. This is an indication that one of the principal stress axes is in alignment with the wave generated by the oriented tranducer. Such an oriented transducer can be fabricated according to the art utilizing shaped coils (such as shown in FIG. 9-11) to create oriented driving forces in the material being tested.

Numerous variations and modifications may be made without departing from the present invention. Accordingly, it should be clearly understood that the form of the present invention described above and shown in the accompanying drawings is illustrative only and is not intended to limit the scope of the present invention.

What is claimed is:

1. A method of measuring stress in a material comprising the steps of:
   a) obtaining a correlation between the difference in velocity of orthogonally polarized transverse waves in the material and stress in the material;
   b) simultaneously applying a plurality of differently oriented driving forces to the surface of the material from a single electromagnetic transducer;
   c) allowing said driving forces to radiate orthogonally polarized transverse waves through the material;
   d) determining the difference in velocity between said orthogonally polarized transverse waves; and
   e) comparing said difference in velocity to said correlation, whereby stress can be measured in said material.

2. The method as claimed in claim 1 wherein said step of applying driving forces comprises applying said forces in a plurality of radially oriented directions.

* * * * *